(12) United States Patent
Zan et al.

(10) Patent No.: US 8,723,503 B2
(45) Date of Patent: May 13, 2014

(54) VERTICAL TYPE SENSOR

(75) Inventors: Hsiao-Wen Zan, Hsinchu (TW);
Hsin-Fei Meng, Hsinchu (TW);
Ming-Zhi Dai, Hsinchu (TW);
Yu-Chiang Chao, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 308 days.

(21) Appl. No.: 13/009,440

(22) Filed: Jan. 19, 2011

(65) Prior Publication Data

US 2012/0086431 A1   Apr. 12, 2012

(30) Foreign Application Priority Data

Oct. 11, 2010 (TW) ................. 99134543 A

(51) Int. Cl.
| | | |
|---|---|---|
| *H01L 29/08* | (2006.01) | |
| *H01L 21/00* | (2006.01) | |
| *G01N 33/543* | (2006.01) | |
| *H01L 51/52* | (2006.01) | |
| *H01L 51/05* | (2006.01) | |
| *G01N 27/414* | (2006.01) | |

(52) U.S. Cl.
CPC ...... *G01N 33/54373* (2013.01); *G01N 33/5438* (2013.01); *H01L 51/5203* (2013.01); *H01L 51/057* (2013.01); *G01N 27/414* (2013.01)
USPC ............. 324/76.11; 257/40; 438/49

(58) Field of Classification Search
CPC .......... G01N 33/54373; G01N 33/5438; G01N 27/414; H01L 51/5203; H01L 51/057
USPC .................. 324/76.11; 250/40, 50
See application file for complete search history.

(56) References Cited

U.S. PATENT DOCUMENTS

| | | | |
|---|---|---|---|
| 2002/0020853 A1 | 2/2002 | Nakashima et al. | |
| 2002/0092342 A1 | 7/2002 | Samman et al. | |
| 2007/0141580 A1* | 6/2007 | David et al. ................. | 435/6 |
| 2009/0113992 A1 | 5/2009 | Hunter et al. | |
| 2009/0230384 A1* | 9/2009 | Meng et al. ................. | 257/40 |
| 2009/0272433 A1* | 11/2009 | Morooka et al. ............. | 136/256 |
| 2010/0237885 A1* | 9/2010 | Meng et al. ................. | 324/717 |

FOREIGN PATENT DOCUMENTS

TW         098108545      10/2010

OTHER PUBLICATIONS

Wang et al., "Hydrogen-selective sensing at room temperature with ZnO nanorods", Applied Physics Letters, vol. 86, 243503 (2005).
Razi et al., "Investigation of hydrogen sensing properties and aging effects of Schottky like Pd/porous Si", Sensors and Actuators B: Chemical, 146, pp. 53-60 (2010).

* cited by examiner

*Primary Examiner* — Melissa Koval
*Assistant Examiner* — Farhana Hoque
(74) *Attorney, Agent, or Firm* — Edwards Wildman Palmer LLP; Peter F. Corless; Steven M. Jensen

(57) ABSTRACT

The present invention provides a vertical type sensor, including a substrate; a first electrode formed on the substrate; a sensing layer formed on the first electrode layer and reactive to a target substance, wherein the first electrode layer is interposed between the substrate and the sensing layer; and a second electrode layer formed on the sensing layer and having a plurality of openings, wherein the sensing layer is interposed between the first electrode layer and the second electrode layer, and the target substance contacts the sensing layer via the plurality of openings. The vertical type sensor of the present invention provides instant, sensitive and rapid detection.

19 Claims, 8 Drawing Sheets

VERTICAL TYPE SENSOR

CROSS-REFERENCES TO RELATED APPLICATIONS

This application claims under 35 U.S.C. §119(a) the benefit of Taiwanese Application No. 99134543, filed Oct. 11, 2010, the entire contents of which is incorporated herein by reference.

BACKGROUND OF THE INVENTION

1. Field of the Invention

The present invention relates to sensors, and more particularly, to a vertical type sensor.

2. Description of Related Art

In the field of medical therapy, it is a trend to develop a sensor, such as a sensor for detecting biological molecules. Particularly, in order to achieve instant measurement and monitor chronic diseases, it is the major trend to develop a detecting method which has high sensitivity, instant and precise detection, and reproducibility.

U.S. Patent Application Publication No. 20020092342 discloses a gas sensor, as shown in FIG. 10, including a back electrode 71, a SiC semiconductor layer 72 formed on the back electrode 71, an aluminum nitride layer 73 formed on the SiC semiconductor layer 72, and a gate electrode 74 formed on the aluminum nitride layer 73. The gate electrode 74 is a porous catalytically active metal electrode for forming an ionized product after the reaction of the target gas and the gate electrode 74, and then the ionized product diffuses to an interface of the aluminum nitride layer 73 and the gate electrode 74, so as to change potential distribution and voltage shift, thereby achieving the detection. Similarly, U.S. Patent Application Publication No. 20020020853 and U.S. Patent Application Publication No. 20090113992 disclose the usage of catalytically active metals.

In addition, H. T. Wang et al., APPLIED PHYSICS LETTERS 86, 243503 (2005) and F. Razi et al., Sensors and Actuators B: Chemical 146 (2010) 53-60 disclose a horizontal type sensors. In H. T. Wang et al., the zinc oxide pillar is formed by vapor deposition, and then the position of the electrode is defined. The gas concentration is identified by the horizontal type sensor based on the change of resistance; however, the stability of such horizontal type sensor is not so satisfied due to the significant variation of pillar distribution. In the horizontal type sensor of F. Razi et al., the substrate is made of porous p-typed silicon, and palladium is deposited on the silicon substrate, wherein hydrogen is trapped by palladium, and the porous silicon substrate is used for carrying palladium rather than detecting the target gas. Further, the metal electrodes, made of different materials, of the horizontal type sensor are identified by photolithography, such that the fabrication is complicated.

Therefore, there is a need to develop a sensor with high sensitivity, instant measurement, easy-to-read signal and reproducibility.

SUMMARY OF THE INVENTION

The present invention provides a vertical type sensor including a substrate; a first electrode layer formed on the substrate; a sensing layer formed on the first electrode layer, wherein the first electrode is interposed between the substrate and the sensing layer, and the sensing layer is made of a material reactive to a target substance or has a portion reactive to a target substance; and a second electrode layer formed on the sensing layer, wherein the sensing layer is interposed between the first electrode layer and the second electrode layer, the second electrode layer has a plurality of openings, and the target substance contacts the sensing layer via the openings of the second electrode layer.

In an aspect of the present invention, the sensing layer has a first porous structure with openings upwards corresponding to the openings of the second electrode layer.

In an aspect of the present invention, the vertical type sensor of the present invention further includes a semiconductor layer inactive to the target substance, and the semiconductor layer is disposed on the top or bottom of the sensing layer. In addition, the sensing layer has openings upwards corresponding to the openings of the second electrode layer. The semiconductor layer can also have a second porous structure with openings upwards corresponding to the openings of the second electrode layer.

In an aspect of the present invention, the sensing layer includes a plurality of sensing sublayers. For example, a first, second and third sensing sublayers are sequentially formed on the first electrode layer. In addition, in one embodiment, the first and second sensing sublayers respectively have a third porous structure with openings aligned upwards, and the third sensing sublayer has a fourth porous structure formed randomly. Alternatively, the first sensing sublayer has a third porous structure with openings upwards, and the second and third sensing sublayers have openings upwards corresponding to the openings of the second electrode layer.

The present invention further provides a method for forming a vertical type sensor. The method includes the steps of providing a substrate with a surface formed with a first electrode layer thereon; forming a sensing layer on the first electrode layer, wherein the sensing layer is reactive to a target substance; applying a plurality of first nanoparticles on the sensing layer in a manner that a portion of a top surface of the sensing layer is exposed from the plurality of first nanoparticles; forming a second electrode layer on the exposed portion of the top surface of the sensing layer, wherein the sensing layer is interposed between the first electrode layer and the second electrode layer; and removing the plurality of first nanoparticles to form a plurality of openings in the second electrode layer for exposing the sensing layer, wherein the target substance contacts the sensing layer via the plurality of openings.

In one embodiment of the present invention, the method further includes the step of removing a part of the sensing layer for forming a plurality of openings in the sensing layer upwards corresponding to the openings of the second electrode layer.

In an aspect of the present invention, the method further includes the step of forming an inert semiconductor layer on the first electrode layer before forming the sensing layer. Alternatively, the method further includes the step of forming an inert semiconductor layer on the first electrode layer before applying the plurality of first nanoparticles. In addition, after removing the plurality of first nanoparticles, the method further includes the step of removing a certain portion of the sensing layer and the inert semiconductor layer by using the second electrode layer as a mask, such that the sensing layer has openings upwards corresponding to the openings of the second electrode layer, and the inert semiconductor layer has a second porous structure with openings upwards corresponding to the openings of the second electrode layer.

In the method of the present invention, the sensing layer can have openings formed randomly.

In an aspect of the present invention, the sensing layer includes a plurality of sensing sublayers. For example, a first, second and third sensing sublayers are sequentially formed on the first electrode layer. In addition, in one embodiment, the first and second sensing sublayers respectively have a third porous structure with openings aligned upwards, and the third sensing sublayer has a fourth porous structure formed randomly. Alternatively, the first sensing sublayer has a third porous structure with openings upwards, and the second and third sensing sublayers have openings upwards corresponding to the openings of the second electrode layer. The third porous structure is formed by the steps of applying a plurality of nanoparticles on the first electrode layer to expose a portion of the first electrode layer; forming a material reactive to the target substance on the portion of the first electrode layer; and removing the plurality of nanoparticles to form the third porous structure. The openings of the second and the third sensing sublayers are formed by using the second electrode layer as a mask and removing a part of the second and the third sensing sublayers after removing the plurality of nanoparticles.

The present invention further provides a method for forming a vertical type sensor, includes the steps of providing a substrate having a surface formed with a first electrode layer; forming a first sensing sublayer on the first electrode layer; applying a plurality of nanoparticles on the first sensing sublayer to expose a portion of the first sensing sublayer; forming sequentially a second sensing sublayer, a third sensing sublayer and a second electrode layer on the portion of the first sensing sublayer; removing the nanoparticles to form openings of the second electrode layer for exposing the first sensing sublayer, wherein the target substance contacts the first, the second and the third sensing sublayers.

The present invention further provides a detecting method, including the steps of applying a bias voltage to the first electrode layer and the second electrode layer of the vertical type sensor of the present invention to form current; providing the target substance to contact the sensing layer of the vertical type sensor; and measuring a change of electrical property of the vertical type sensor.

The present invention further provides a detecting system, including a vertical type sensor of the present invention; a voltage supply device electrically connected to the first electrode layer and the second electrode layer of the vertical type sensor for providing a bias voltage to the vertical type sensor; and a detecting device electrically connected to the vertical type sensor for measuring a change of electrical property of the vertical type sensor.

In a preferred embodiment, the change of electrical property is a change of current.

The vertical type sensor of the present invention has instant measurement, and high sensitivity. Furthermore, the vertical type sensor of the present invention provides a change of current for detection, such that expensive detecting equipments are not needed so as to decrease cost and be used for large-scale screening.

DETAILED DESCRIPTION OF THE PREFERRED EMBODIMENTS

The detailed description of the present invention is illustrated by the following specific examples. Persons skilled in the art can conceive the other advantages and effects of the present invention based on the disclosure contained in the specification of the present invention.

In the present invention, the structure, scale and size shown in drawings are provided for persons skilled in the art to understand the disclosure of the present invention rather than limiting the practice of the present invention. The present invention covers any modifications, variations and adjustments of the structures which achieve effects and purposes of the present invention. In addition, the terms, such as "on", "top", "bottom", and "one", herein are used for illustrating the present invention rather than limiting the scope of the present invention.

The First Embodiment

Referring to FIG. 1A to FIG. 1D, a method for forming a vertical type sensor of the present invention is shown.

Figure 1A:
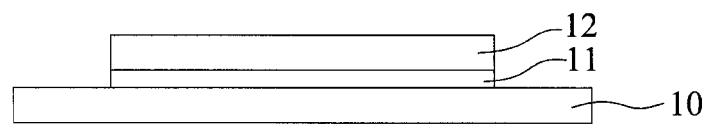
FIG. 1A to FIG. 1D are schematic views showing the method for forming the vertical type sensor according to the present invention.

As shown in FIG. 1A, a first electrode layer 11, such as indium tin oxide, is formed on a surface of a substrate 10, and a sensing layer 12 is formed on a surface of the first electrode layer 11. The sensing layer 12 is made of a material reactive to a target substance or the sensing layer 12 has a portion reactive to a target substance. The portion of the sensing layer 12 is made of an inert material such as semiconductor material, conductive material or insulating material and the portion (a receptor, for example) of the sensing layer 12 is a binding or a contact to the inert material. For example, the sensing layer 12 may have a probe group for binding or contacting the inert material. The probe group is one or more selected from the group consisting of —OH, —CHO, —COOH, —SO$_3$H, —CN, —NH$_2$, —SH, —COSH, —COOR and a halide. In addition, the probe group may be a biological molecule selected from the group consisting of a nucleic acid, an antibody, an antigen, a polysaccharide, a protein, an amino acid, and an enzyme.

For example, the probe group is biotin. Biotin has specific binding to its substrate such as avidin, and thus the vertical type sensor of the present invention is capable of specifically detecting the presence of avidin in the target substance.

The sensing layer can be made of a semiconductor material, which is one or more selected from the group consisting of In—Ga—Zn—O (IGZO), zinc oxide ($ZnO_x$), titanium dioxide and indium oxide. The above illustrated probe group may bind to or contact the semiconductor material, conductive material or insulating material.

In one embodiment, the sensing layer may be, but not limited to, an organic polymer semiconductor, such as

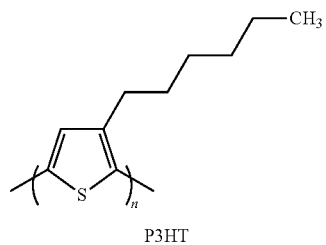

P3HT

Usually, the organic polymer semiconductor can be formed as the sensing layer by spin coating. Alternatively, the sensing layer may be formed from other materials by deposition.

Figure 1B:
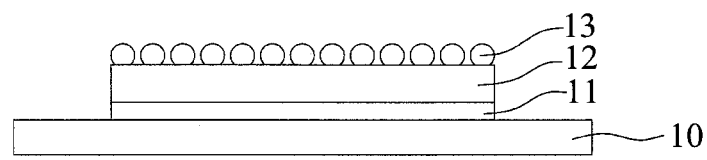

As shown in FIG. 1B, a plurality of nanoparticles 13 having a diameter of 200 nm are applied on the sensing layer 12 by immersing. The nanoparicles may be polystyrene beads. Preferably, the nanoparticles 13 are applied as a single layer to expose a portion f the top surface of the sensing layer 12.

Figure 1C:
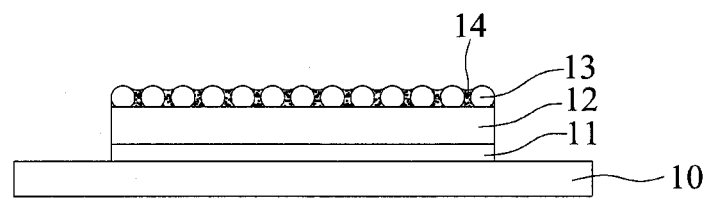

As shown in FIG. 1C, a second electrode layer 14, such as aluminum, is formed on the exposed surface of the sensing layer 12 by sputtering, such that the sensing layer 12 is interposed between the first electrode layer 11 and the second electrode layer 14.

Figure 1D:
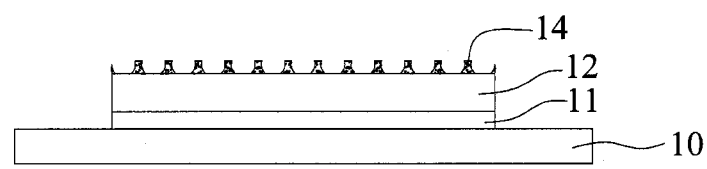

As shown in FIG. 1D, the nanoparticles 13 are removed by using an adhesive tape, such that openings 141 are formed in the second electrode layer 14 to expose the sensing layer 12, such that the target substance is allowed to contact the sensing layer 12.

According to the above illustrated method, the vertical type sensor of the present invention includes a substrate 10; a first electrode layer 11 formed on the substrate 10; a sensing layer 12 formed on the first electrode layer 11, wherein the first electrode layer 11 is interposed between the substrate 10 and the sensing layer 12, and the sensing layer 12 is made of a material reactive to a target substance or the sensing layer 12 has a portion reactive to a target substance; and a second electrode layer 14 formed on the sensing layer 12 such that the sensing layer is interposed between the first electrode layer 11 and the second electrode layer 14, and the second electrode layer 14 has a plurality of openings 141 for the target substance to contact the sensing layer 12.

The Second Embodiment

Figure 2:
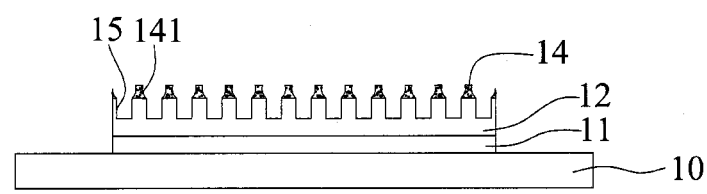
FIG. 2 is a schematic view showing a cross-section of another vertical type sensor according to the present invention.

Referring to FIG. 2, another vertical type sensor of the present invention is illustrated.

As shown in FIG. 2, the present embodiment is similar to the first embodiment except that after removing the nanoparticles 13, a portion of the sensing layer 12 is removed by using the second electrode layer 14 as a mask and using oxygen plasma, such that a first porous structure 15 is formed and has openings upwards corresponding to the openings 141 of the second electrode layer 14.

Hence, the sensing layer 12 of the vertical type sensor has a first porous structure 15 with openings upwards corresponding to the openings 141 of the second electrode layer 14.

Referring to FIG. 3A to FIG. 3F, another vertical type sensor of the present invention is shown.

As shown in FIG. 3A to FIG. 3D, the present embodiment is similar to the first embodiment except an additional inert semiconductor layer 16.

Figure 3A:
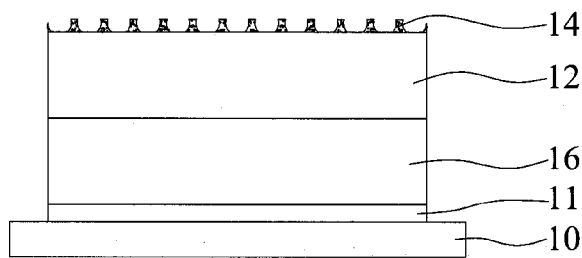
FIG. 3A to FIG. 3D are schematic views showing a vertical type sensor having an inert semiconductor layer according to the present invention.

As shown in FIG. 3A, before forming the sensing layer 12, an inert semiconductor layer 16 is formed on the first electrode layer 11. The semiconductor layer 16 of the vertical type sensor is disposed at the bottom surface of the sensing layer 12 and inactive to the target substance.

Figure 3B:
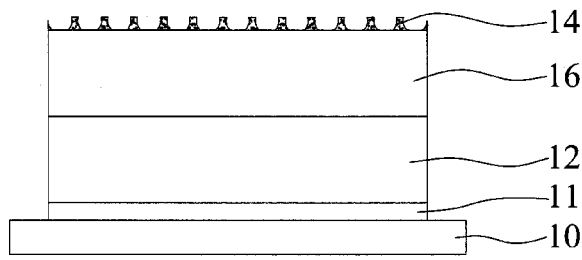
Figure 3C:
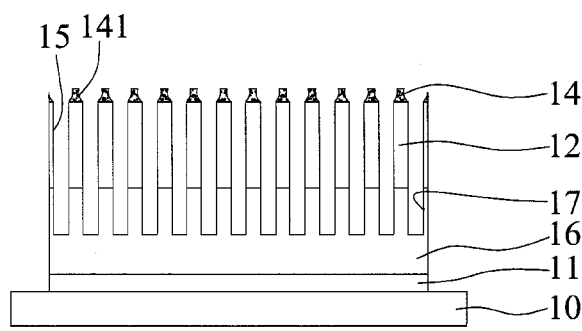
Figure 3D:
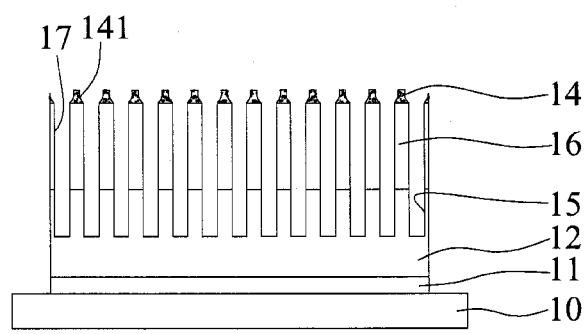

As shown in FIG. 3B, before the nanoparticles are applied as illustrated in FIG. 1B, the inert semiconductor layer 16 is formed on the sensing layer 12. Thus, the inert semiconductor layer 16 is formed on the top surface of the sensing layer 12. As shown in FIG. 3C and FIG. 3D, after the process shown in FIGS. 3A and 3B that forming the second electrode layer 14 is formed and the nanoparticles 13 are removed, is performed, a portion of the sensing layer 12 and the inert semiconductor layer 16 are removed by using the second electrode layer 14 as a mask, such that the sensing layer 12 has openings upwards corresponding to the openings 141 of the second electrode layer 14, similar to the first porous structure 15, and the inert semiconductor layer 16 has a second porous structure 17 with openings upwards corresponding to the openings 141 of the second electrode layer 14.

The Fourth Embodiment

Figure 4:
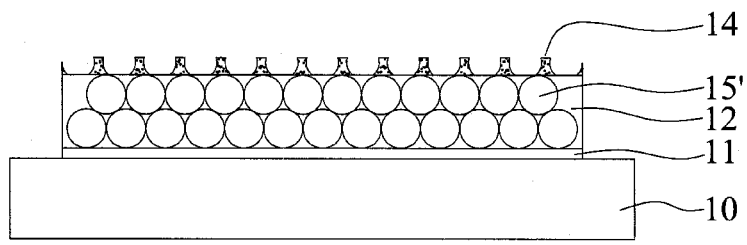
FIG. 4 is a schematic view showing a vertical type sensor according to the present invention.

Referring to FIG. 4, another vertical type sensor of the present invention is shown. The vertical type sensor of the present embodiment is similar to that of FIG. 1D except that the sensing layer 12 has openings 15' formed randomly. The openings 15' are formed by the way similar to the above illustration except that the polystyrene beads are stacked for several layers on the first electrode layer 1, the material reactive to the target substance is filled in the space between the polystyrene beads, and after removing the polystyrene beads, the sensing layer 12 has the openings 15' formed randomly. Taiwan Patent No. 98108545 discloses the formation of the porous sensing layer which is incorporated herein as reference. In addition, the porous sensing layer can be formed by electric spinning.

The Fifth Embodiment

Figure 5A:
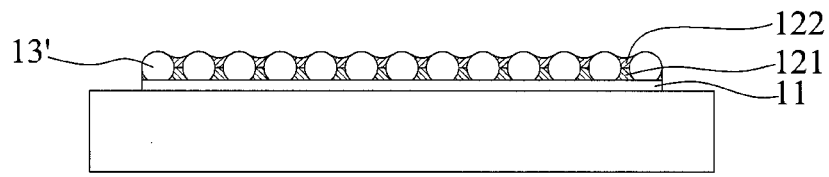
FIG. 5A to FIG. 5C are schematic views showing a vertical type sensor and a method for forming the vertical type sensor according to the present invention.
Figure 5B:
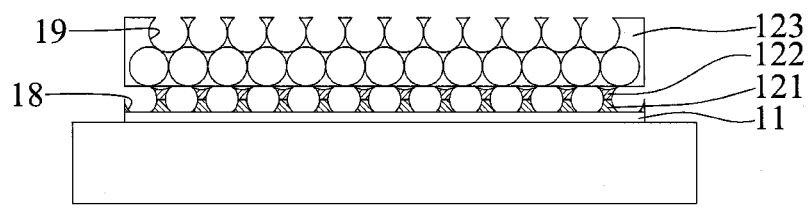
Figure 5C:
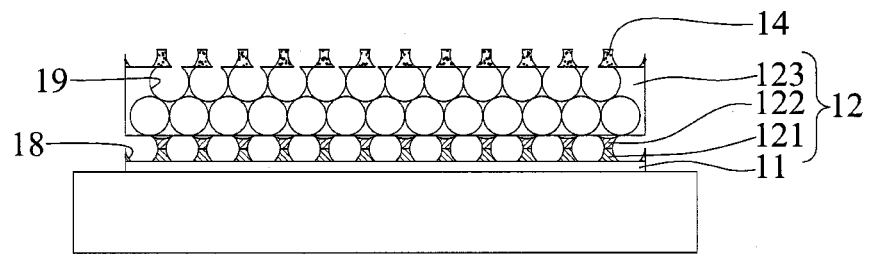

Referring to FIG. 5A to FIG. 5C, another vertical type sensor of the present invention is shown.

In the present embodiment, the sensing layer of the vertical type sensor includes a plurality of sensing sublayers. For example, the sensing layer 12 includes a first sensing sublayer 121, a second sensing sublayer 122, and a third sublayer 123 sequentially formed on the first electrode layer. The first sensing sublayer 121 and the second sensing sublayer 122 have a third porous structure 18 with openings aligned upwards, and the third sensing sublayer 123 has a fourth porous structure 19 formed randomly.

As shown in FIG. 5A, the third porous structure 18 is formed by the steps of applying a single layer 13' of nanoparticles on the first electrode layer 11 in a manner that a portion of the surface of the first electrode layer 11 is exposed from the single layer 13' of nanoparticles; forming the material or the portion reactive to the target substance on the exposed surface of the first electrode layer 11, wherein the materials of the first sensing sublayer 121 and the second sensing sublayer 122 are different; and removing the single layer 13' of nanoparticles, so as to form a third porous structure 18.

As shown in FIG. 5B and FIG. 5C, the fourth porous structure 19 is formed by the way illustrated in the fourth embodiment, and then a second electrode layer 14 is formed, so as to obtain the vertical type sensor of the present invention.

The Sixth Embodiment

Figure 6A:
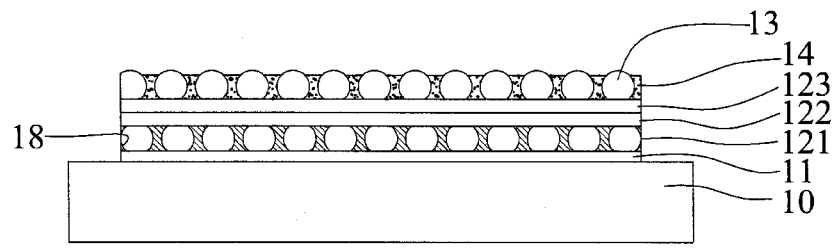
FIG. 6A to FIG. 6B' are schematic views showing a vertical type sensor and a method for forming the vertical type sensor according to the present invention, wherein FIG. 6A' and FIG. 6B' provides the method different from that shown in FIG. 6A and FIG. 6B, respectively.
Figure 6B:
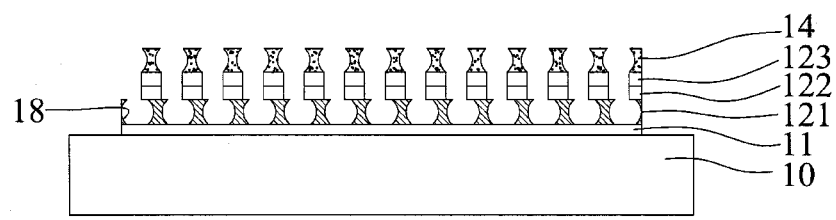
Figure 6A:
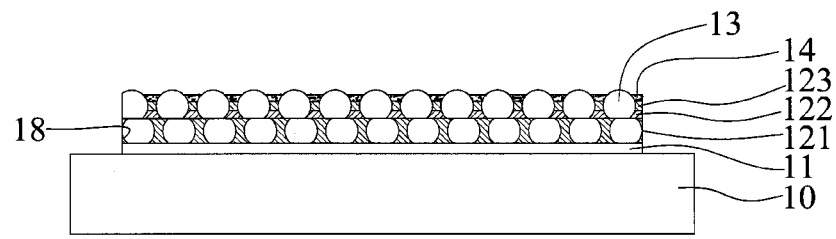
Figure 6B:
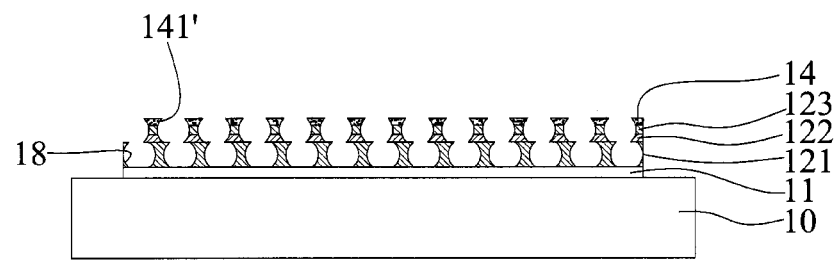

Referring to FIG. 6A to FIG. 6B, another vertical type sensor of the present invention is illustrated.

In the present embodiment, the sensing layer of the vertical type sensor includes a first sensing sublayer 121, a second sensing sublayer 122 and a third sublayer 123, wherein the first sensing sublayer 121 has a third porous structure 18 with openings upwards, and the second sensing sublayer 122 and the third sensing sublayer 123 have openings upwards corresponding to the openings 141 of the second electrode layer 14.

As shown in FIG. 6A and FIG. 6B, the first sensing sublayer 121 is formed by the way illustrated in the fifth embodiment. Before applying the nanoparticles 13, the second sensing sublayer 122 and the third sensing sublayer 123 are formed, and after forming the second electrode layer 14 and removing the nanoparticles, a portion of the second sensing sublayer 122 and that of the third sensing sublayer 123 are removed by using the second electrode layer 14 as a mask.

As shown in FIG. 6A' and FIG. 6B', the present invention provides another method for forming a second sensing sublayer 122 and a third sensing sublayer 123. Before forming the second electrode layer 14 as shown in FIG. 1B, the second sensing sublayer 122 and the third sensing sublayer 123 are sequentially formed on the exposed portion of the top surface of the first sensing sublayer 121. Then, the nanoparticles are removed, such that the second electrode layer 14 has openings for exposing the first sensing sublayer 121. Thus, the target substance contacts the first sensing sublayer 121, the second sensing sublayer 122 and the third sublayer 123.

In the vertical type sensor having a first sensing sublayer 121, a second sensing sublayer 122 and a third sublayer 123, it is preferable to have at least one sensing sublayer reactive to the target substance.

The Seventh Embodiment

Figure 7:
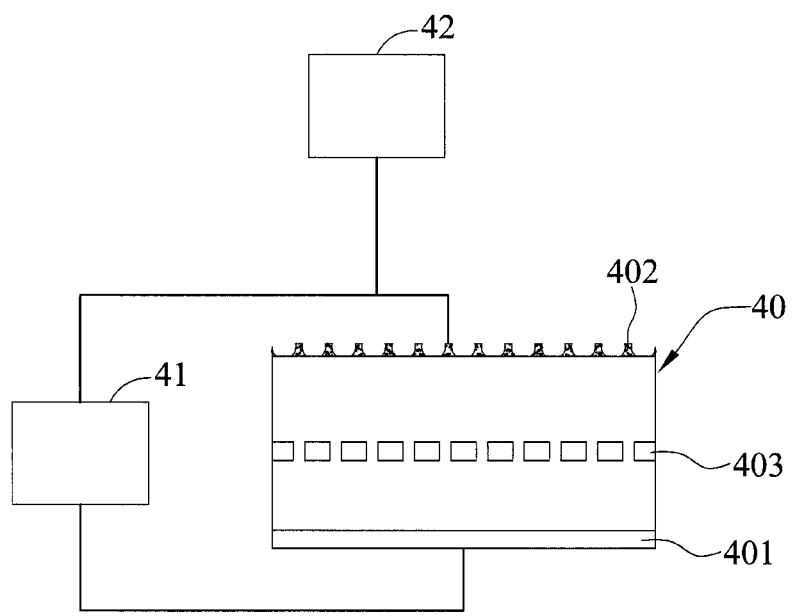
FIG. 7 is a schematic view showing a detecting system having a vertical type sensor of the present invention.

Referring to FIG. 7, a detecting system including the vertical type sensor of the present invention is shown.

As shown in FIG. 7, the detecting system includes a vertical type sensor 40 of the present invention; a voltage supply device 41 electrically connected to a first electrode layer 402 and a second electrode layer 402 of the vertical type sensor 40 for providing a bias voltage to the vertical type sensor 40; and a detecting device 42 electrically connected to the vertical type sensor 40 for measuring a change of electrical property of the vertical type sensor 40.

When a vertical type sensor with a plurality of sensing sublayers is used in a detecting system, and one of the sensing sublayers is electrically conductive, the voltage supply device can be electrically connected (by a conductive wire, for example) to such sensing sublayer. Similarly, while in detecting, a bias voltage may be applied to the sensing sublayer, and then the change of electrical property of the vertical type sensor is measured. In addition, the vertical type sensor of the present invention may further include a third electrode layer 403 embedded in the sensing layer. Preferably, the third electrode layer 403 has a gate structure, and is formed by patternization process or using nanoparticles as illustrated in the above. The voltage supply device may also be electrically connected to the third electrode layer 403 to provide more detection data.

Test

Figure 8A:
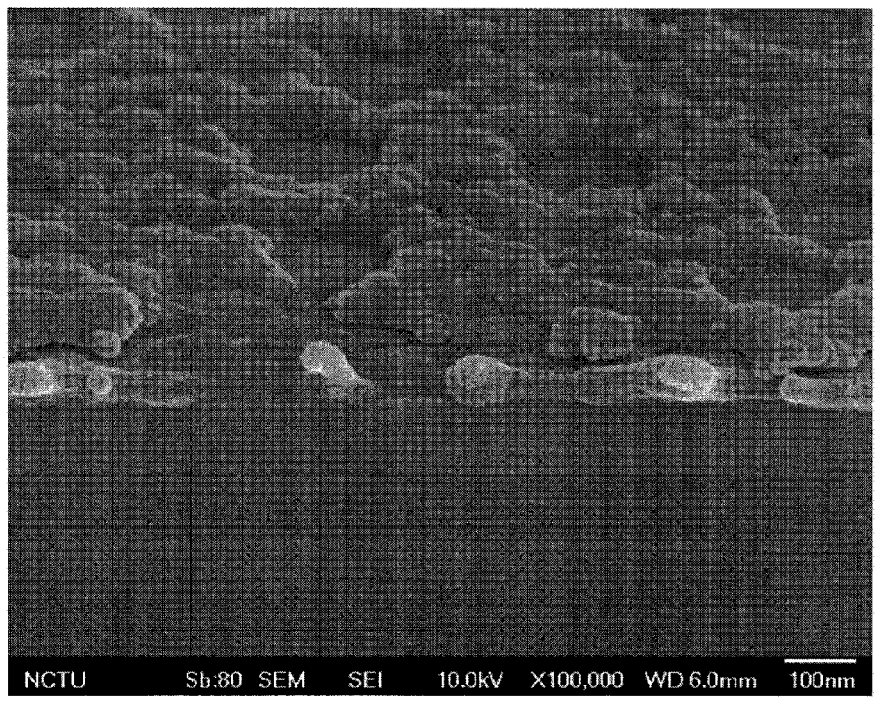
FIG. 8A and FIG. 8B are diagrams showing the vertical type sensor of the present invention having an aluminum electrode with a plurality of openings, and the vertical type sensor of the present invention having a sensing layer with a first porous structure, respectively, by scanning electron microscopy.
Figure 8B:
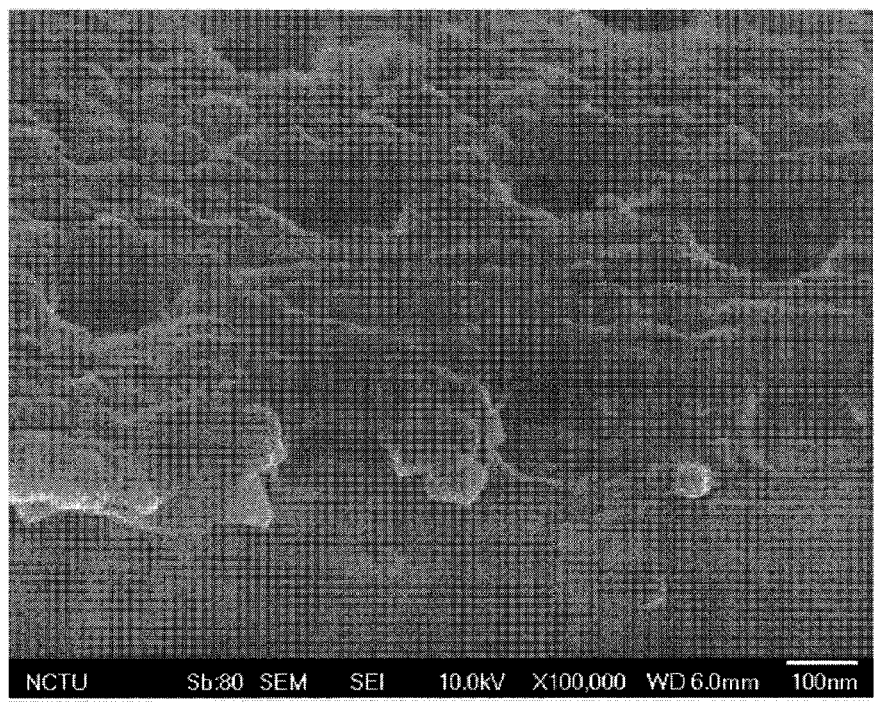

In the vertical type sensor formed in the second embodiment of the present invention, the first electrode layer is made of indium tin oxide, the sensing layer is made of P3HT (poly (3-hexylthiophene-2,5-diyl)), which is an organic semiconductor material reactive to ammonia and has a thickness of 60 nm, and the second electrode layer is made of aluminum and has a thickness of 40 nm FIG. 8A shows that the aluminum electrode has a plurality of openings, and FIG. 8B shows the sensing layer of the vertical type sensor of the present invention has a first porous structure.

In the control group, the vertical type sensor is formed by the way similar to that illustrated in the first embodiment of the present invention except that no nanoparticles are used, such that the second electrode layer of the vertical type sensor of the control group has no openings.

In the test, the vertical type sensor of the present invention and the vertical type sensor of the control group are respectively placed in nitrogen environment, voltage is applied to the vertical type sensor of the present invention and the vertical type sensor of the control group, then ammonia is introduced into the nitrogen environment, and the release of the gas is controlled.

Figure 9A:
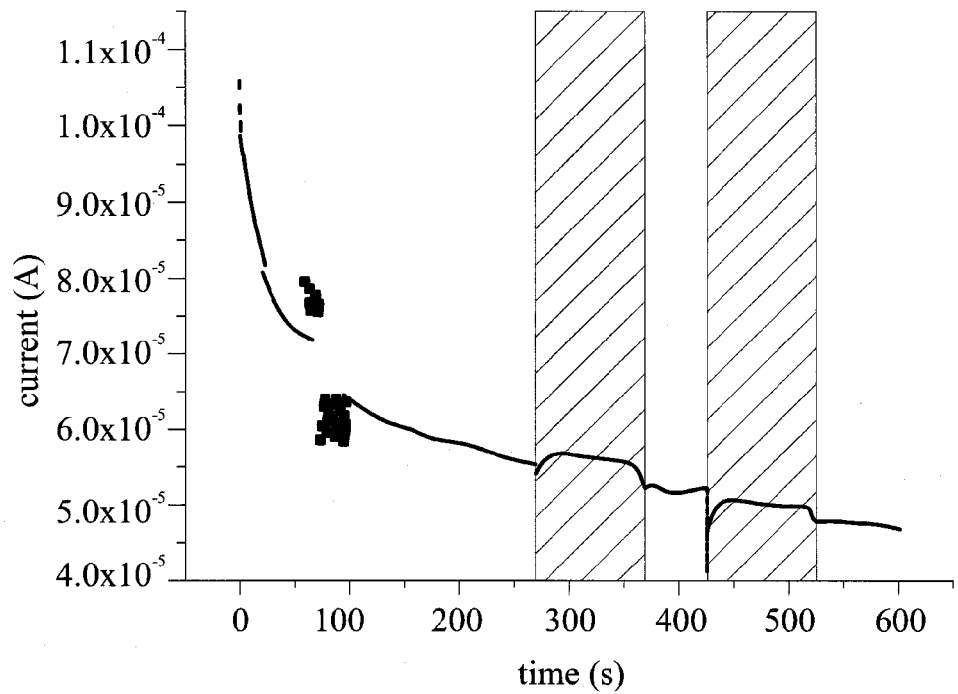
FIG. 9A to FIG. 9C are images showing a change of current of a vertical type sensor according to the present invention.
Figure 9B:
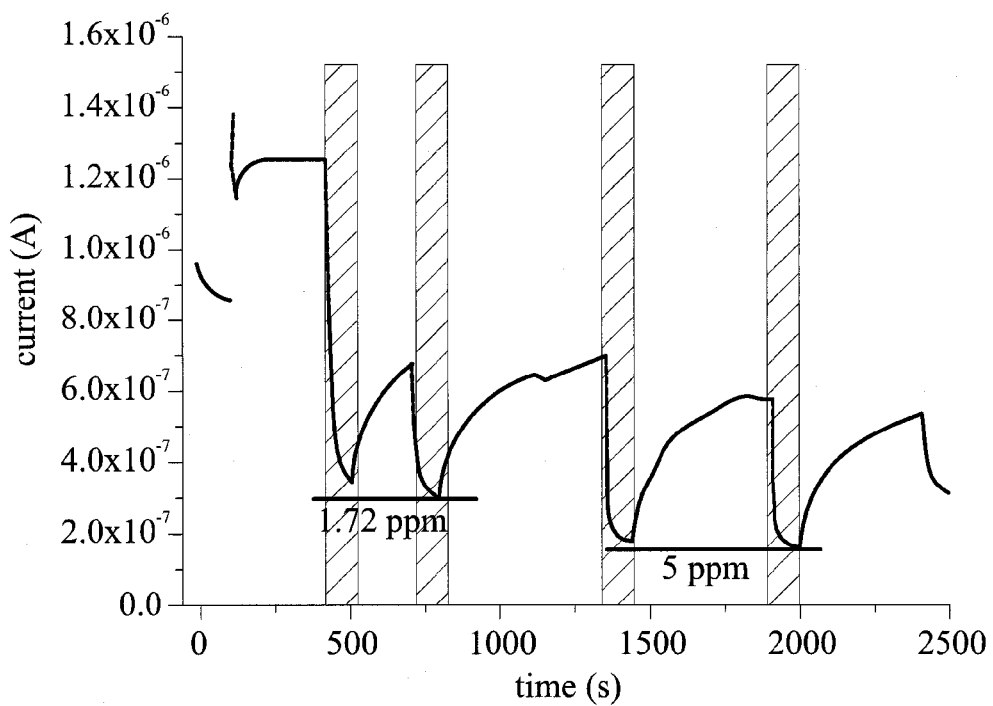
Figure 9C:
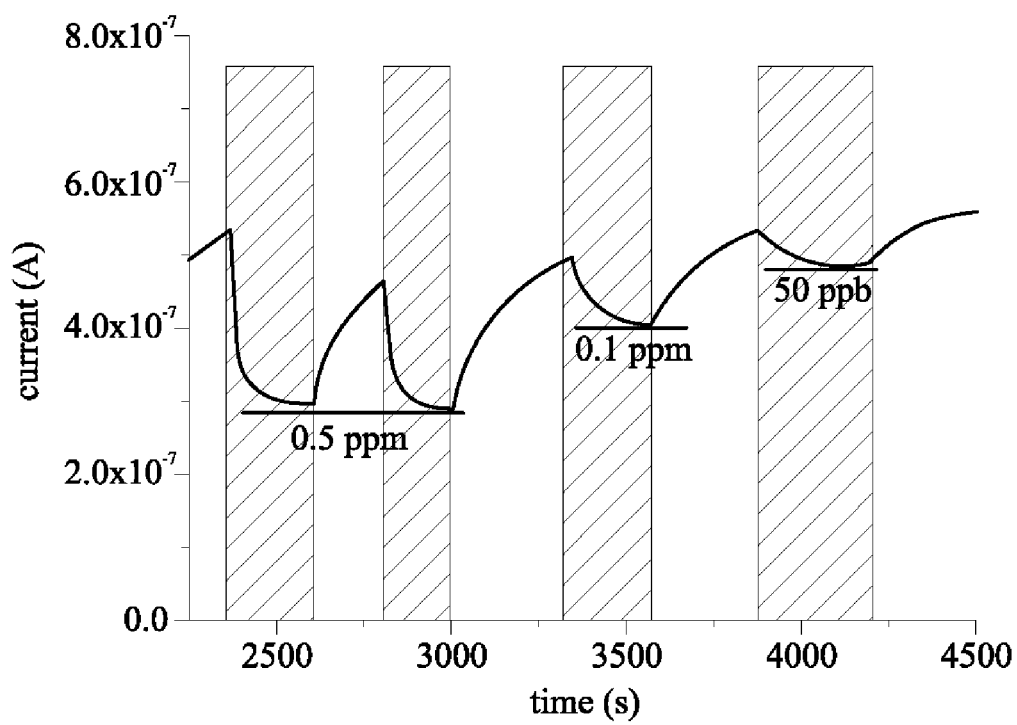
Figure 10:
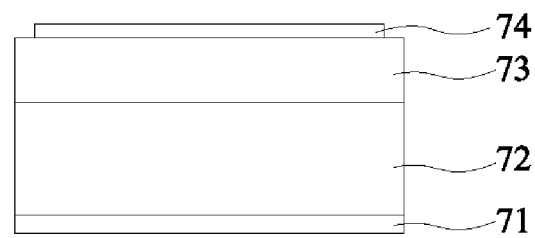
FIG. 10 is a schematic view showing a gas sensor disclosed in U.S. Patent Application Publication No. 20020092342.

FIG. 9A is a diagram showing the current change of the vertical type sensor of the control group while introducing 5 ppm of ammonia, wherein there is some, but not significant, current change at time 270 to 370 second and at time 430 to 520 second. In contrast, FIG. 9B shows that the vertical type sensor of the present invention has significant current change while introducing 1.72 ppm and 5 ppm of ammonia. In addition, while introducing 0.5 ppm of ammonia, the vertical type sensor of the present invention also has significant current change, as shown in FIG. 9C. Accordingly, the vertical type sensor is much more sensitive due to having a second electrode layer with openings or a sensing layer having a corresponding first porous structure. Especially, after repetitive use, the vertical type sensor of the present invention still has satisfactory sensitivity. In addition, the sensitivity of the detection is reduced to about 0.05 ppm.

In the present invention, the second electrode layer with openings is formed by using nanoparticles rather than photolithography process. The method of the present invention provides a controllable porous structure (such as the openings of the second electrode layer or the first and second porous structures). Hence, the method of the present invention is simple and provides a sensor with high reproducibility. In addition, the vertical type sensor of the present invention has high sensitivity, instant measurement, fast operation, and no need to be applied with high voltage.

Furthermore, the porous structure with openings upwards, especially aligned with the openings of the second electrode layer, has an uniform structure, and thus has faster recovery in response to the reversible sensing layer or prove group.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

The invention claimed is:

1. A vertical type sensor, comprising: a substrate; a first electrode layer formed on the substrate;
   a sensing layer formed on the first electrode layer and reactive to a target substance, wherein the first electrode layer is interposed between the substrate and the sensing layer; and
   a second electrode layer formed on the sensing layer and layer having a plurality of openings so as to expose the sensing layer via the openings, wherein the sensing layer is interposed between the first electrode layer and the second electrode layer, and the target substance contacts the sensing layer via the plurality of openings.

2. The vertical type sensor of claim 1, wherein the sensing layer has openings formed randomly or a first porous structure.

3. The vertical type sensor of claim 2, wherein the first porous structure of the sensing layer has openings upwards corresponding to the openings of the second electrode layer.

4. The vertical type sensor of claim 1, further comprising a semiconductor layer being inert to the target substance and disposed on the top or bottom of the sensing layer.

5. The vertical type sensor of claim 4, wherein the sensing layer has openings upwards corresponding to the openings of the second electrode layer.

6. The vertical type sensor of claim 5, wherein the semiconductor layer has a second porous structure with openings upwards corresponding to the openings of the second electrode layer.

7. The vertical type sensor of claim 1, wherein the sensing layer comprises a plurality of sensing sublayers.

8. The vertical type sensor of claim 7, wherein the sensing layer comprises a first, a second and a third sensing sublayers sequentially formed on the first electrode layer.

9. The vertical type sensor of claim 8, wherein the first and the second sensing sublayers respectively have a third porous structure with openings aligned upwards, and the third sensing sublayer has a fourth porous structure formed randomly.

10. The vertical type sensor of claim 8, wherein the first sensing sublayer has a third porous structure with openings upwards, and the second and the third sensing sublayers respectively have openings upwards corresponding to the openings of the second electrode layer.

11. The vertical type sensor of claim 1, wherein the sensing layer has a portion reactive to the target substance, and the portion of the sensing layer is a probe group.

12. The vertical type sensor of claim 11, wherein the probe group comprises one or more selected from the group consisting of —OH, —CHO, —COON, —SO$_3$H, —CN, —NH$_2$, —SH, —COSH, —COOR and a halide.

13. The vertical type sensor of claim 11, wherein the probe group is a biological molecule selected from the group consisting of a nucleic acid, an antibody, an antigen, a polysaccharide, a protein, an amino acid, and an enzyme.

14. The vertical type sensor of claim 1, further comprising a third electrode layer embedded in the sensing layer.

15. A detecting system, comprising:
   a vertical type sensor of claim 1;
   a voltage supply device electrically connected to the first electrode layer and the second electrode layer of the vertical type sensor for providing a bias voltage to the vertical type sensor; and
   a detecting device electrically connected to the vertical type sensor for measuring a change of electrical property of the vertical type sensor.

16. A method for forming a vertical type sensor, comprising the steps of:
   providing a substrate having a surface formed with a first electrode layer thereon;
   forming a sensing layer on the first electrode layer, wherein the sensing layer is reactive to a target substance;
   applying a plurality of first nanoparticles on the sensing layer in a manner that a portion of a top surface of the sensing layer is exposed from the plurality of first nanoparticles;
   forming a second electrode layer on the portion of the top surface of the sensing layer wherein the sensing layer is interposed between the first electrode layer and the second electrode layer; and
   removing the plurality of first nanoparticles and forming a plurality of openings in the second electrode layer so as to expose the sensing layer via the openings, wherein the target substance contacts the sensing layer via the plurality of openings.

17. The method of claim 16, wherein the sensing layer has a portion reactive to the target substance, and the portion of the sensing layer is a probe group, wherein the probe group comprises one or more selected from the group consisting of —OH, —CHO, —COON, —SO$_3$H, —CN, —NH$_2$, —SH, —COSH, —COOR and a halide, or the probe group is a biological molecule selected from the group consisting of a nucleic acid, an antibody, an antigen, a polysaccharide, a protein, an amino acid, and an enzyme.

18. The method of claim 16, wherein the sensing layer is made of a semiconductor material which is one or more metal oxides selected from the group consisting of zinc oxide, titanium dioxide, and indium oxide.

19. The method of claim 16, further comprising the step of removing a part of the sensing layer for forming a plurality of openings in the sensing layer upwards corresponding to the openings of the second electrode layer.

* * * * *